United States Patent
Gusakov et al.

[11] Patent Number: 5,961,484
[45] Date of Patent: Oct. 5, 1999

[54] METHOD FOR REMOVAL OF MEDICAL DEVICE, ESPECIALLY A TRANSDUCER PATCH

[75] Inventors: Ignaty Gusakov, Aurora; George T. Bauer, Williamsville, both of N.Y.

[73] Assignee: Graphic Controls Corporation, Buffalo, N.Y.

[21] Appl. No.: 09/012,705

[22] Filed: Jan. 23, 1998

Related U.S. Application Data

[62] Division of application No. 08/813,002, Mar. 4, 1997, Pat. No. 5,848,966.

[51] Int. Cl.$^6$ .............................. A61N 1/30; A61B 5/04
[52] U.S. Cl. .......................... 604/20; 600/372; 600/392; 600/394; 607/152
[58] Field of Search ..................... 600/372, 386, 600/391, 392, 394–397; 607/149, 152, 153, 115; 604/20, 21; 424/448

[56] References Cited

U.S. PATENT DOCUMENTS

| | | |
|---|---|---|
| 3,295,515 | 1/1967 | Kahn . |
| 3,387,608 | 6/1968 | Figar . |
| 3,420,223 | 1/1969 | Day et al. . |
| 3,590,810 | 7/1971 | Kopecky . |

(List continued on next page.)

FOREIGN PATENT DOCUMENTS 410009 of 1934 United Kingdom .

OTHER PUBLICATIONS

1995 Graphic Controls Corporation Brochure: "Graphic Controls Neurodiagnostic Monitoring Products".
1995 Graphic Controls Corporation Brochure for "BioTac ® ECG Conductive Adhesive Electrode".
1994 Graphic Controls Corporation Brochure for "Offset Dx™, S'Offset® ECG Electrodes".
1994 Graphic Controls Corporation Brochure for "Medi–Trace® Pediatric Electrodes".
Instructions for Habitrol™ Nicotine Transdermal System, BASEL Pharmaceuticals, Division of Ciba–Geigy.
Fries et al., "Pressure Sensitive Adhesives for Medical Applications", National Starch and Chemical Corporation (1984).

(List continued on next page.)

*Primary Examiner*—Wynn Wood Coggins
*Assistant Examiner*—Sharon Finkel
*Attorney, Agent, or Firm*—Ratner & Prestia

[57] ABSTRACT

An electrode for attachment to a patient comprises a flexible planar member, an electrically conductive member embedded in said flexible member and adapted for contact with the patient, a layer of electrically conductive adhesive applied to the conductive member and the flexible planar member on a side of the flexible planar member facing the patient. Through holes extend completely through the electrode and, optionally, may also extend through the layer of adhesive. Alternatively, a permeable electrode having a permeable member which allows a solvent to pass through to the adhesive may be used to eliminate the need for through holes in the electrode. The permeable electrode may also be coated with sodium chloride or potassium chloride and used in conjunction with an applicator containing an alcohol gel which liquefies upon contact with the sodium chloride or potassium chloride. A transdermal patch comprises a layer or compartment where the medication is stored and a layer of adhesive through which the medication diffuses. Again, a plurality of through holes are formed completely through the product and, optionally, through the adhesive as well. An applicator containing the solvent can be placed in direct contact with the top of the electrode or the top of the transdermal patch. In this manner, the solvent can be directed through the through holes formed in either the electrode or the patch to release the solvent and to facilitate its removal.

11 Claims, 8 Drawing Sheets

U.S. PATENT DOCUMENTS

| | | |
|---|---|---|
| 4,004,578 | 1/1977 | Palmius . |
| 4,066,078 | 1/1978 | Berg . |
| 4,367,755 | 1/1983 | Bailey . |
| 4,384,582 | 5/1983 | Watt . |
| 4,422,461 | 12/1983 | Glumac . |
| 4,695,277 | 9/1987 | Lauk ................................... 604/304 |
| 4,699,146 | 10/1987 | Sieverding . |
| 4,921,475 | 5/1990 | Sibalis . |
| 4,947,853 | 8/1990 | Hon . |
| 4,947,865 | 8/1990 | Hon et al. . |
| 5,070,880 | 12/1991 | Gomez et al. . |
| 5,124,076 | 6/1992 | Smuckler . |
| 5,135,477 | 8/1992 | Untereker et al. .................... 604/20 |
| 5,158,537 | 10/1992 | Haak et al. ........................... 604/20 |
| 5,167,613 | 12/1992 | Karami et al. . |
| 5,203,768 | 4/1993 | Haak et al. ........................... 604/20 |
| 5,250,022 | 10/1993 | Chien et al. . |
| 5,271,940 | 12/1993 | Cleary et al. ....................... 424/448 |
| 5,279,544 | 1/1994 | Gross et al. . |
| 5,310,404 | 5/1994 | Gyory et al. ......................... 604/20 |
| 5,326,570 | 7/1994 | Rudnic et al. . |
| 5,374,241 | 12/1994 | Lloyd et al. . |
| 5,390,675 | 2/1995 | Sheehan et al. . |
| 5,406,945 | 4/1995 | Riazzi et al. . |
| 5,520,180 | 5/1996 | Uy et al. . |
| 5,582,587 | 12/1996 | Gyory et al. ......................... 604/20 |
| 5,628,729 | 5/1997 | Okabe ................................... 604/20 |
| 5,645,527 | 7/1997 | Beck ..................................... 604/20 |
| 5,738,647 | 4/1998 | Bernhard et al. ..................... 604/20 |

OTHER PUBLICATIONS

1996 Physicians' Desk Reference, pp. 322, 1550–1553, for Nicotrol® Transdermal Nicotine Patch, Pharmacia AB Corporation.

1996 Physicians' Desk Reference, pp. 322, 1518–1523, and Instructions for Nicoderm® System, Merrell Dow Pharamaceuticals.

METHOD FOR REMOVAL OF MEDICAL DEVICE, ESPECIALLY A TRANSDUCER PATCH

This application is a division of application Ser. No. 08/813,002, filed Mar. 4, 1997, now U.S. Pat. No. 5,848,966, issued Dec. 15, 1998.

FIELD OF THE INVENTION

The present invention relates, in general, to medical devices (such as medical electrodes and transdermal patches) which are attached to a patient's skin. In particular, a medical electrode and transdermal patch are each disclosed which have features that enable them to be easily removed from the skin of a patient. A method of easily removing such medical devices is also disclosed.

BACKGROUND OF THE INVENTION

Medical electrodes and transdermal patches are well known in the art. Many types of medical electrodes have been introduced in recent years. Typically they comprise: (1) a metallic or electrically conductive carbon terminal member electrically connected to an electro-medical apparatus such as an electrocardiograph; (2) an adhesive tape or pad for holding the terminal member in place on the skin; and (3) an electrically conductive conformable interfacing material such as electrolyte gel or paste over the surface of the terminal member which contacts the skin to reduce skin impedance and to improve electrical contact between the skin and the terminal member. The adhesive may be introduced into the electrically conductive material.

Medical electrodes should not be confused with sensor support bases. Such bases are described, for example, in U.S. Pat. No. 4,947,853, No. 4,947,865, and No. 5,070,880. Such support devices are used in conjunction with Doppler transducers and, hence, are not dependent on electrical conductivity to obtain proper readings. The No. '853 patent and the No. '865 patent relate, for example, to devices for monitoring the contractions of a patient in labor. The No. '880 patent relates to a stabilization device for supporting a transcranial Doppler transducer housing adjacent to the temporal bone of the head. This is useful, for example, for obtaining accurate blood flow velocity measurements. Because none of these devices depend on electrical conductivity to obtain proper readings, the use of an adhesive which is electro-conductive to secure these devices to the patient is completely unnecessary.

Various devices are also known in the art for delivering medication to a patient transdermally. Iontophoretic devices for delivering ionized drugs through the skin have been known since the early 1900's. U.K. Patent No. 410,009 (1934) describes an iontophoretic device which is powered by a galvanic cell and which includes a material containing the drug to be delivered transdermally. The galvanic cell produces the current necessary for iontophoretically delivering the drug.

Today, iontophoresis is not limited solely to the delivery of ions (e.g., drug ions) into the body by means of electric current. For example, it is now recognized that iontopheric delivery devices can be used to deliver an uncharged drug or agent into the body. This is accomplished by a process called electro-osmosis. Electro-osmosis is the transdermal flux of a liquid solvent (e.g., the liquid solvent containing the uncharged drug or agent) which is induced by the presence of an electric field imposed across the skin by the donor electrode. As used herein, the terms "iontopheresis" and "ionopheretic" refer to one or more of (1) the delivery of charged drugs or agents by electromigration, (2) the delivery of uncharged drugs or agents by the process of electro-osmosis, (3) the delivery of charged drugs or agents by the combined processes of electromigration and electro-osmosis, and (4) the delivery of a mixture of charged and uncharged drugs or agents by the combined processes of electromigration and electro-osmosis.

Other transdermal patches do not require electrical power for proper operation. An example of such an item is the Nicotrol transdermal nicotine patch product (Nicotrol is a registered trademark of the Pharmacia AB Corporation). This patch comprises two distinct layers. The layer nearest the patient's skin is a combination of a non-woven polyester and a polyisobutylene and polybutene adhesive. Covering this layer is an impermeable laminated polyester backing layer. This backing layer prevents evaporation of nicotine from, or transmission of light to, the nicotine-containing layer beneath. A layer of adhesive is applied on the impermeable backing layer. The non-woven polyester layer is placed over the adhesive and another adhesive layer is applied over the polyester. The two adhesive layers penetrate the polyester (non-uniformly) to form a single adhesive/polyester composite layer. The nicotine is introduced by printing it on the non-woven polyester layer before the second application of adhesive. Once the patch is applied, the nicotine diffuses out of the adhesive/polyester layer and into the skin of the patient. As sold, the patch includes a release layer which protects the adhesive and which is removed before applying the patch to the skin of the patient.

The removal of medical electrodes or transdermal patches from the skin of patients risks discomfort or pain. A clinician can apply a specific solvent, such as isopropyl alcohol, to help remove the electrode from the skin painlessly. An eye dropper can be used to wet the skin-adhesive boundary while the user simultaneously lifts the edge of the electrode. This approach is slow and cumbersome and it requires a skilled person. The reason for these disadvantages is that the solvent reaches only a small portion of the adhesive at a time and, because the solvent penetrates slowly, the whole process of removal is slow. The uneven distribution of the solvent at the edge of the electrode while lifting it might cause pain to the patient.

SUMMARY OF THE INVENTION

An electrode for attachment to a patient comprises a flexible planar member, an electrically conductive member embedded in the flexible member and adapted for contact with the patient, and a layer of electrically conductive adhesive applied to the conductive member and to the flexible planar member on a side of the flexible planar member facing the patient. Through holes extend completely through the flexible planar member to the layer of adhesive and may also, optionally, extend through the adhesive layer. Alternatively, a permeable electrode having a permeable member which allows a solvent to pass through to the adhesive may be used to eliminate the need for through holes in the electrode. The permeable electrode may also be coated with sodium chloride or potassium chloride and used in conjunction with an applicator containing an alcohol gel which liquefies upon contact with the sodium chloride or potassium chloride. A transdermal patch comprises a layer or compartment where the medication is stored and a layer of adhesive through which the medication diffuses. Again, a plurality of through holes are formed completely through to the adhesive and, optionally, through the adhesive as well. An applicator containing the solvent can be placed in direct contact with the top of the electrode or the top of the transdermal patch. In this manner, the solvent can be directed through the through holes formed in either the electrode or the patch to facilitate its removal.

DETAILED DESCRIPTION

The present invention relates to the use of medical devices having through holes or permeable members (such as electrodes and transdermal patches) which are attached with adhesive to a patient's skin. By applying a solvent through the through holes or permeable members, the adhesive is dissolved or neutralized and removal of the medical device from the patient's skin is facilitated.

Figure 1:
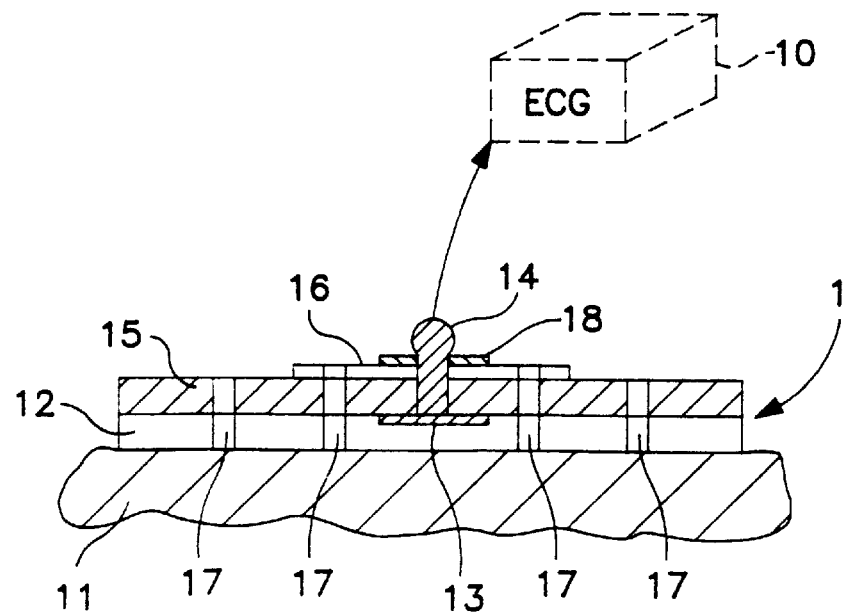
FIG. 1 is a cross-sectional side view of an electrode in accordance with a first exemplary embodiment of the present invention.

A first embodiment of the present invention is shown in FIG. 1. FIG. 1 is a cross-sectional side view (not drawn to scale) of a medical electrode 1 in accordance with an exemplary embodiment of the present invention. The medical electrode 1 shown in FIG. 1 is used to make electrical contact between the patient's skin 11 and an appropriate device 10 used for acquisition of medical data (e.g., an ECG or the like). Eyelet 13 is embedded in planar member 15 which, preferably, is made of a flexible material such as foam polymer. A label 16 typically is placed on the top of planar member 15. Stud 14 is in contact with eyelet 13 and engages flange 18 to sandwich planar member 15 and label 16 thereby securing stud 14 in place. Electrical wires are attached between stud 14 and the medical data acquisition device 10. Electrode 1 includes an electrically conductive adhesive 12 which covers eyelet 13 and is placed on the side of planar member 15 which faces skin 11 of a patient. The electrically conductive adhesive 12 assures that electrode 1 is held in place on the patient's skin 11. In this way, the required electrical conductivity between the patient's skin 11 and eyelet 13 is obtained.

Figure 2:
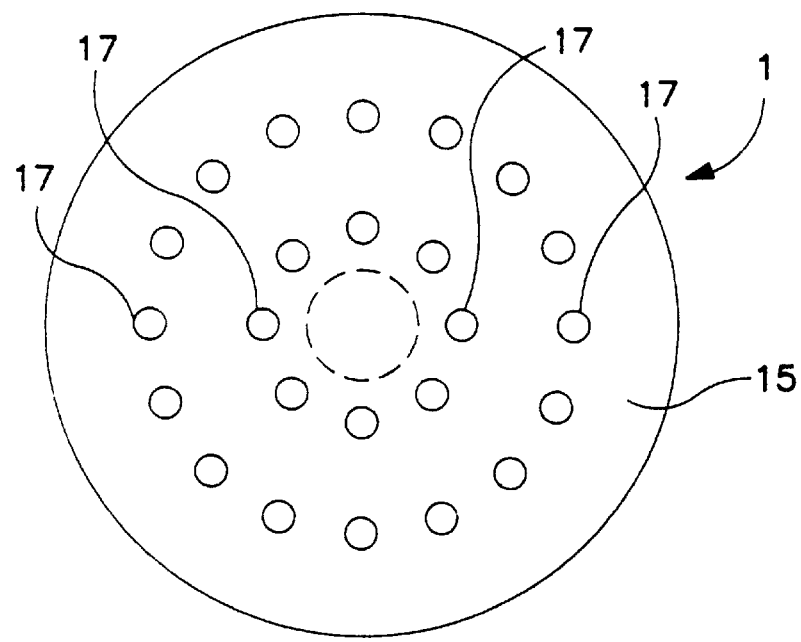
FIG. 2 is a bottom view of the electrode shown in FIG. 1.

Through holes 17 are also formed in electrode 1. As shown in FIG. 2, holes 17 are formed in multiple locations throughout planar member 15. Also, as shown in FIG. 1, these through holes may be formed through conductive adhesive 12 (although this is not required for some applications). The size, shape, and number of holes depend on numerous factors, including the size of the electrode and the material and thickness of the adhesive. The size of the holes typically ranges between 0.1 to 10 mm in diameter. The number of holes typically ranges between 4 to 100. The greater the number of holes or the greater the size of the holes, the easier it is for the solvent to reach the adhesive and dissolve or neutralize the adhesive. It is also desirable, however, to optimize the number and size of the holes to assure that there is adequate adhesion between the electrode and the patient's skin.

It may be desirable, given a certain sized electrode, to vary the number and size of holes until an appropriate level of adhesion and removal ease is obtained. The inventors have found, for example, for a 40 mm diameter electrode, a total of 25 holes of 0.3 mm diameter are desirable. Although an increased number of holes will facilitate the removal of the adhesive, it is understood that the applicator of the present invention is not limited for use with electrodes having any specified number of holes. As will be readily recognized by those having ordinary skill, the present invention may be used with electrodes such as the neonatal Model 1801 PELLET FOAM™ electrode having four throughholes and manufactured by Graphic Controls Corporation, Buffalo, N.Y.

Typical materials for the adhesive are described, for example, in U.S. Pat. No. 5,124,076. The adhesive is of sufficient thickness to adhere the electrode to the patient's skin (typically 0.2–0.5 mm). Each of these numbers is desirably selected to assure that the holes do not interfere with the mechanical and electrical properties of the electrode.

Figure 3A:
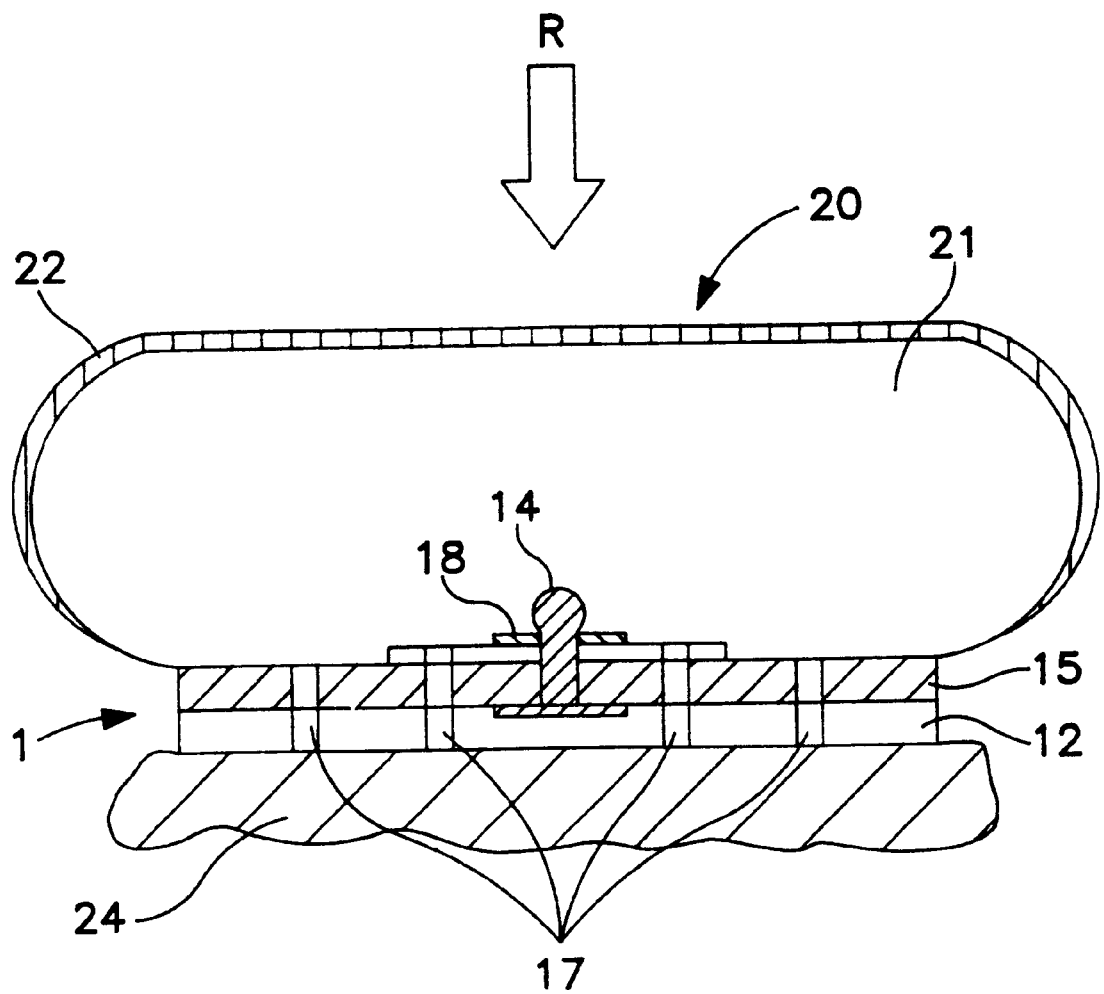
FIG. 3A is a cross-sectional side view illustrating the use of an applicator to facilitate electrode removal in accordance with an exemplary embodiment of the present invention.
Figure 3B:
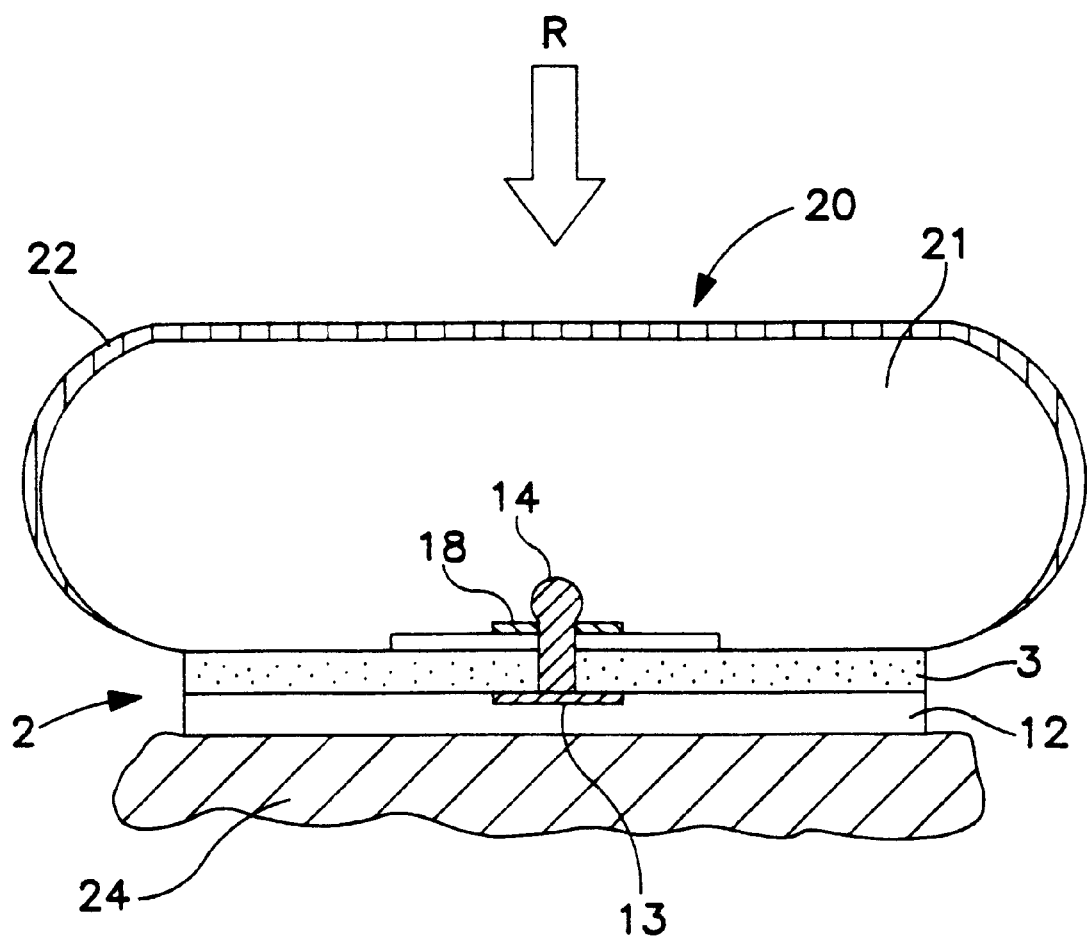
FIG. 3B is a cross-sectional side view illustrating the use of an applicator to facilitate electrode removal in accordance with another exemplary embodiment of the present invention.

Shown in FIGS. 3A and 3B is an applicator 20 comprising absorbent dispensing material 21 which contains a solvent or adhesive-neutralizing material. Dispensing material 21 may comprise a sponge or cloth material such as felt, cotton, a non-woven material (e.g., Rayon), or foam which is saturated with a solvent (e.g., isopropyl alcohol, acetone, or water) or other adhesive-neutralizing material. Dispensing material 21 is partly surrounded with a thin, flexible, plastic layer 22. As shown in FIG. 3A, by placing the applicator on the top of the electrode 1 and applying pressure in the direction of arrow R on the top of the applicator, the user forces the solvent or adhesive-neutralizing material uniformly and with proper pressure through holes 17 of planar member 15. In this manner, the solvent or adhesive-neutralizing material is placed in contact with the adhesive 12 and, if through holes 17 extend through the adhesive 12, as shown, placed at the interface between adhesive 12 and skin 24.

As shown in FIG. 3B, the applicator may also be used in conjunction with a permeable electrode 2 having conductive adhesive 12 and permeable member 3. Permeable member 3 permits the solvent or adhesive-neutralizing material to penetrate through to adhesive 12 thus eliminating the need for through holes to achieve painless electrode removal from a patient's skin 24. Any electrode having a permeable material which permits penetration by the solvent or adhesive-neutralizing material may be used with applicator 20. Such permeable materials may preferably include, but are not limited to, cloth materials such as felt, cotton, a non-woven material (e.g., Rayon), foam, or GORE-TEX® expanded fiber materials. GORE-TEX® expanded fiber materials are available from W. L. Gore and Associates, Newark, Del. To avoid evaporation of the solvent from dispensing material 21, applicator 20 is desirably kept in a sealed plastic bag when not in use.

Figure 4A:
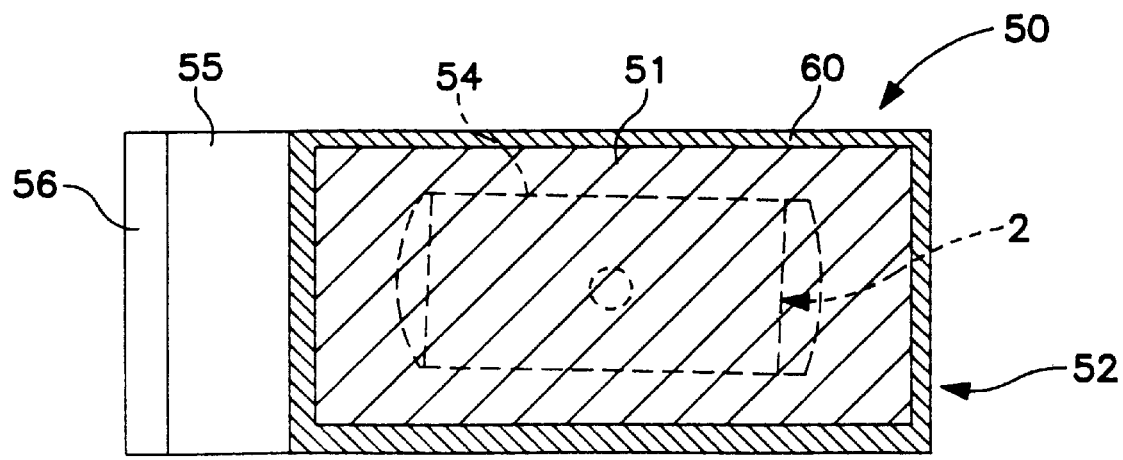
FIG. 4A is a cross-sectional top view illustrating the use of an applicator to facilitate electrode removal in accordance with another exemplary embodiment of the present invention.
Figure 4B:
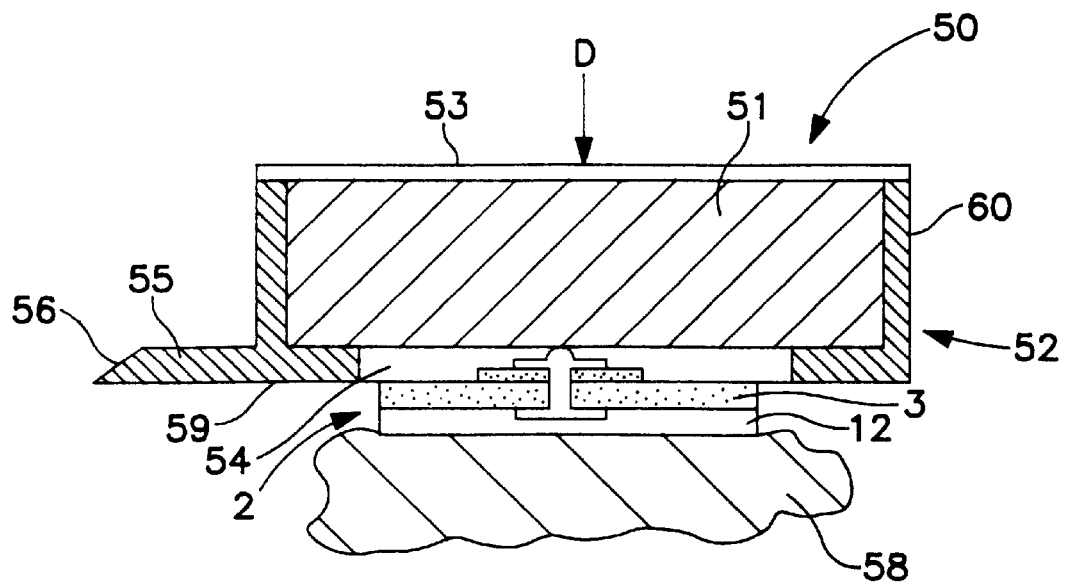
FIG. 4B is a cross-sectional side view illustrating the use of the applicator shown in FIG. 4A to facilitate electrode removal in accordance with the present invention.

Shown in FIGS. 4A and 4B is applicator 50 in accordance with an exemplary embodiment of the present invention which provides for easy and painless removal of permeable electrodes 2 having permeable substrates from the skin. Applicator 50 comprises absorbent dispensing material 51 which contains a solvent or adhesive-neutralizing material. The dispensing material 51 is placed in box 52 and may comprise a sponge or cloth material such as felt, cotton, a non-woven material (e.g., Rayon), or foam which is saturated with a solvent (e.g., isopropyl alcohol, acetone, or water) or other adhesive-neutralizing material. The bottom 59 and sides 60 of box 52 are made of a rigid material such as a thin metal (e.g., aluminum), or a rigid plastic material which, preferably, is moldable (e.g., polypropylene or ABS). The top 53 of box 52 is a membrane made of a flexible material such as a thin elastic rubber or silicon rubber. Located in the bottom 59 of box 52 is an opening 54 which is larger than the permeable electrode 2 to be removed. The bottom 59 of box 52 also includes an extension 55 having a wedge 56.

The procedure for removing permeable electrode 2 from the skin 58 of a patient is as follows. First, opening 54 of applicator 50 is placed over permeable electrode 2 as shown in FIG. 4B. Next, the membrane of top 53 is pushed downward in the direction of arrow D. The applied pressure presses the solvent or adhesive-neutralizing material from dispensing material 51 uniformly and with proper pressure into and through permeable member 3 of permeable electrode 2 and acts to weaken adhesive 12 underneath. Upon lifting applicator 50, wedge 56 is then used to "shave off" electrode 2 from a patient's skin 58. The rigid structure of applicator 50 allows the applicator to be held by hand.

Figure 5A:
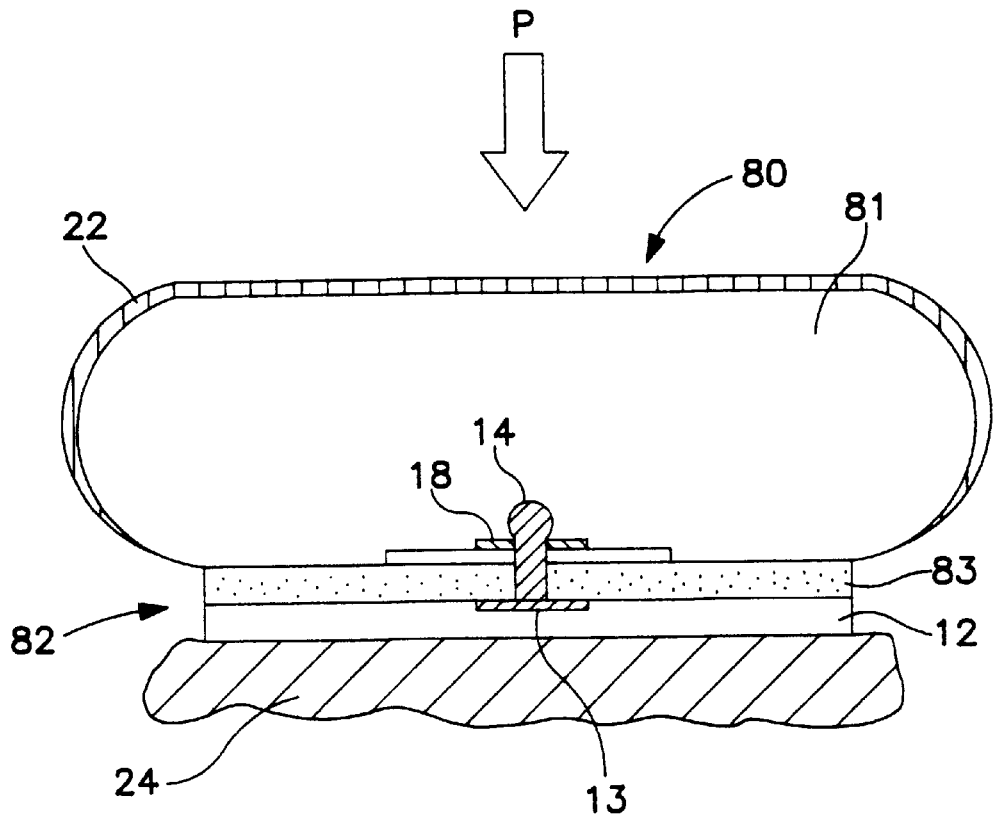
FIG. 5A is a cross-sectional side view similar to that shown in FIG. 3B which illustrates the use of an applicator containing an alcohol gel to facilitate the removal of a permeable electrode coated with sodium chloride or potassium chloride in accordance with another exemplary embodiment of the present invention.
Figure 5B:
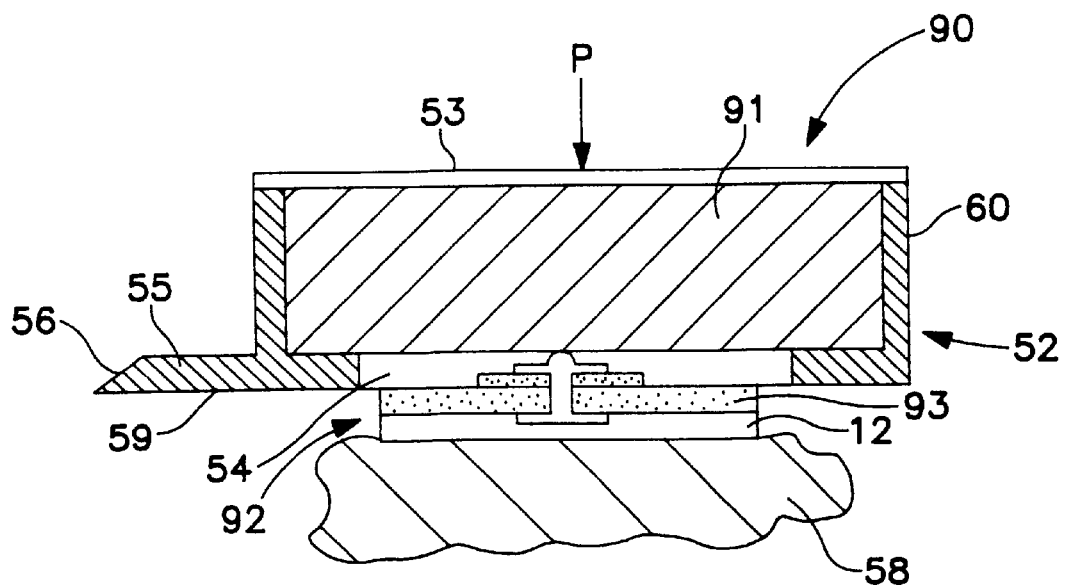
FIG. 5B is a cross-sectional side view similar to that shown in FIG. 4B which illustrates the use of an applicator containing an alcohol gel to facilitate the removal of a permeable electrode coated with sodium chloride or potassium chloride in accordance with another exemplary embodiment of the present invention.

Shown in FIGS. 5A and 5B are applicators 80 and 90, respectively, in accordance with additional exemplary embodiments of the present invention which may be used in conjunction with permeable electrodes 82 and 92, respectively. Permeable electrodes 82 and 92 have permeable members 83 and 93, respectively, which are made preferably of cloth. The permeable members 83 and 93 are treated by applying sodium chloride or potassium chloride, preferably, either during the manufacture of the electrode or immediately before removing the electrode from the skin with the applicator. FIG. 5A shows applicator 80 which corresponds substantially to applicator 20 shown in FIG. 3B but with alcohol gel 81 replacing dispensing material 21. FIG. 5B shows applicator 90 which corresponds substantially to applicator 50 shown in FIG. 4B but with alcohol gel 91 replacing dispensing material 51. Alcohol gels 81 and 91 are exposed along the surfaces of applicators 80 and 90, respectively, which contact permeable members 83 and 93 upon applying pressure in the direction of arrows P as shown in FIGS. 5A and 5B. Upon contact with the sodium or potassium chloride contained in permeable members 83 and 93, the respective alcohol gels 81 and 91 liquefy. The liquefied portion of alcohol gels 81 and 91 then penetrate through permeable members 83 and 93 to contact and weaken the conductive adhesive 12, thereby facilitating removal of permeable electrodes 82 and 92 from a patient's skin. By applying alcohol gel 81 and 91 to permeable electrodes treated in this manner, the sodium or potassium chloride contained in the treated electrode upon contact with the alcohol gel only liquefies that amount of alcohol gel required to convert the salt such that the applicators 80 and 90 can be removed and stored until needed again.

Figure 6A:
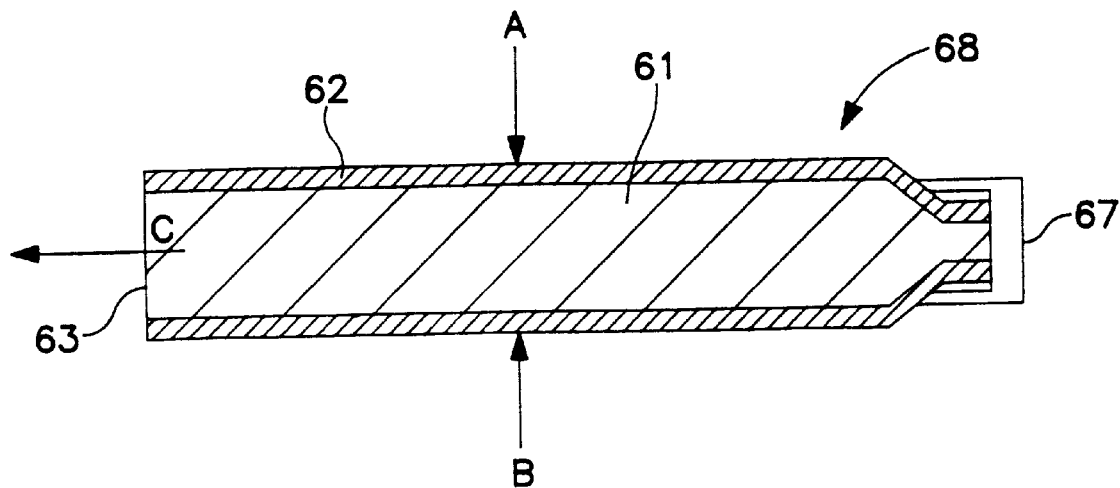
FIG. 6A is a cross-sectional side view illustrating the use of an applicator to facilitate electrode removal in accordance with another exemplary embodiment of the present invention.
Figure 6B:
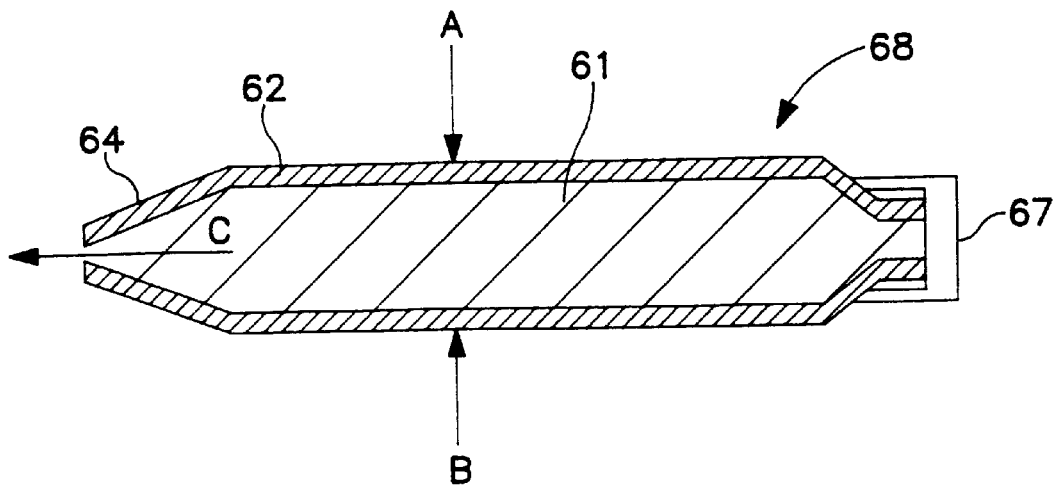
FIG. 6B is a cross-sectional side view illustrating the use of an applicator to facilitate electrode removal in accordance with another exemplary embodiment of the present invention.

Shown in FIGS. 6A and 6B are applicators 68 in accordance with another exemplary embodiment of the present invention which may be used in conjunction with permeable electrodes, preferably of cloth, which have been treated with sodium chloride or potassium chloride. The removal process is illustrated in FIGS. 6A and 6B, in which upon applying pressure in the direction of arrows A and B, alcohol gel 61 is dispensed in the direction of arrow C for application to a treated cloth electrode (not shown) to weaken the electrode adhesive after which the electrode may be easily removed from a patient's skin. The electrodes are treated by applying sodium chloride or potassium chloride to the surface of the electrode, preferably, either during the manufacture of the electrode or immediately before removing it from the skin with the applicator. By applying alcohol gel 61 to the permeable electrodes treated in this manner, the sodium or potassium chloride contained in the treated electrode liquefies the alcohol gel upon contact and permits the liquid to penetrate through the permeable electrode to weaken the electrode adhesive, thereby facilitating removal of the permeable electrode from a patient's skin.

Figure 6C:
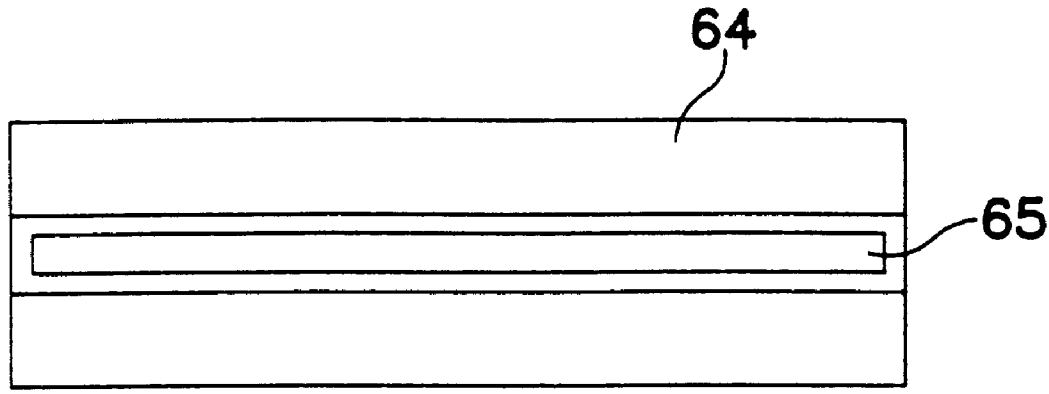
FIG. 6C is a front planar view illustrating an embodiment of the applicator shown in FIG. 6B for facilitating electrode removal in accordance with the present invention.
Figure 6D:
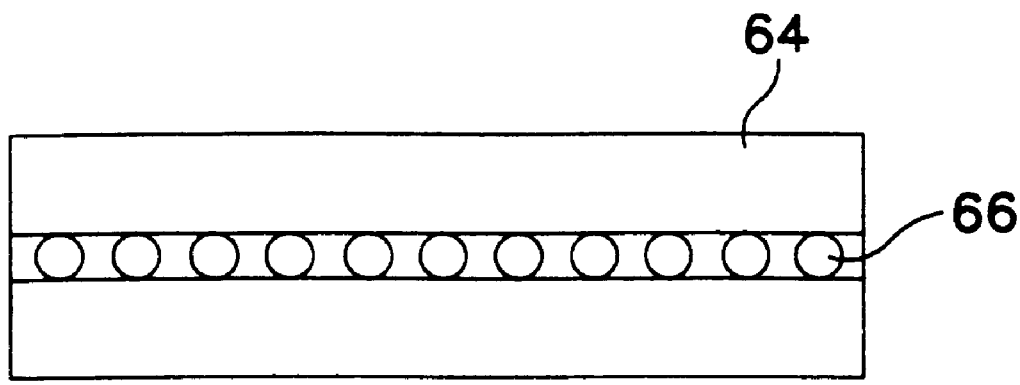
FIG. 6D is a front planar view illustrating another embodiment of the applicator shown in FIG. 6B for facilitating electrode removal in accordance with the present invention.

Such permeable electrodes capable of being used with applicator 68 include permeable electrodes 82 and 92, discussed above, but it is understood that any electrode having a permeable material such as cloth which permits the penetration by the liquefied alcohol may also be used. Such permeable materials may include, but are not limited to, felt, cotton, a non-woven material (e.g., Rayon), foam, or GORE-TEX® expanded fiber materials. GORE-TEX® expanded fiber materials are available from W. L. Gore and Associates, Newark, Del. The applicator 68 shown in FIGS. 6A and 6B may be constructed from a thin tube 62 which is similar in construction to a toothpaste tube and made of a material which is squeezable and selected to provide the desired flexing characteristics. For example, a deformable material such as aluminum is preferred if it is desired that tube 62 remain in a collapsed condition after squeezing. On the other hand, a resilient material such as plastic is preferred if it is desired that tube 62 return to and substantially retain its original shape after squeezing. Tube 62 is filled with an alcohol gel 61 which preferably contains about 75% to 100% alcohol by volume. Tube 62 is closed at one end by a stopper 67 and has an opening 63 at the opposite end for dispensing the alcohol gel 61. The opening of the tube may be formed into a taper 64 as shown in FIG. 6B which may include a slit 65 (as shown in FIG. 6C) or a plurality of holes 66 (as shown in FIG. 6D). By moving the applicator 68 along the top of the electrode and squeezing the tube 62 in the direction of arrows A and B, alcohol gel 61 can be distributed on the surface of a permeable electrode in a controlled manner.

Figure 7:
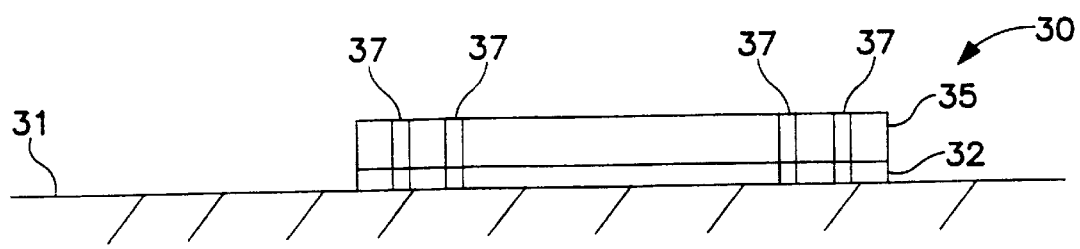
FIG. 7 is a cross sectional side view of a transdermal patch in accordance with an exemplary embodiment of the present invention.

FIG. 7 illustrates an exemplary embodiment of the present invention with regard to transdermal patches. In FIG. 7, a side cross sectional view (not drawn to scale) of transdermal patch 30 is shown. Transdermal patch 30 includes layer 35 in which the medicine to be administered to the patient is located. As with electrode 1 shown in FIG. 3A, an adhesive 32, which need not be conductive, is shown in FIG. 7 which maintains transdermal patch 30 in contact with the patient's skin 31. The medicine diffuses from layer 35 through adhesive 32 and into the patient's skin 31. Again, a desirable number of through holes 37 are formed in transdermal patch 30. Again, the holes may optionally extend through adhesive 32 if desired. Removal of transdermal patch 30 is accomplished by applying an appropriate solvent or adhesive-neutralizing material through the through holes 37 to dissolve or neutralize adhesive 32 at the adhesive-skin interference. An applicator such as applicator 20 shown in FIG. 3A may be used in a similar manner to the manner in which applicator 20 is used to remove a medical electrode.

It is understood that the invention may be used to remove any devices having a permeable structure or construction in conjunction with an adhesive. It is also understood that the invention may be applied to numerous types of transdermal patches including battery-powered patches which use such techniques as iontophoresis for delivering the medicine to the patient. Although the invention has been described in terms of exemplary embodiments, it is contemplated that it may be practiced as outlined above with modifications within the spirit and scope of the appended claims.

What is claimed:

1. An apparatus for delivering medication to a patient, comprising:
   (a) a transdermal patch including:
      a flexible member having a center, a periphery, a side facing the patient, and a plurality of through holes extending through said flexible member and being disposed from the center to the periphery, said flexible member adapted for application of a medication to be administered to the patient through the skin of the patient, and
      an adhesive layer applied to said flexible member on the side facing the patient for attaching said flexible member to the skin of the patient; and
   (b) a removal device including:
      a solution including one of a solvent and an adhesive-neutralizing material, and
      a non-permeable member surrounding said solution;
      wherein said removal device engages said transdermal patch to enable said solution to penetrate said through holes to facilitate removal of said transdermal patch from the patient.

2. The transdermal patch according to claim 1, wherein said plurality of through holes are also formed in said adhesive layer and extend through said adhesive layer.

3. A method of attaching a transdermal patch to the skin of a patient and subsequently removing the patch, comprising the steps of:
   a) attaching the patch to the skin of the patient using an adhesive;
   b) allowing medicine contained by the patch to be administered to the patient;
   c) engaging the patch with a removal device having a solution, including one of a solvent and an adhesive-neutralizing material, and a non-permeable member surrounding the solution;
   d) introducing the solvent through one of a plurality of through holes and a permeable member formed in the patch to release the adhesive; and
   d) removing the patch.

4. The method of attaching a transdermal patch according to claim 3, wherein the plurality of through holes are also formed in the adhesive and extend through the adhesive.

5. The apparatus for delivering medication according to claim 1, wherein said removal device further comprises an absorbent dispensing material with said solution saturated therein.

6. The apparatus for delivering medication according to claim 1, further comprising a wedge coupled to said non-permeable member and adapted to push said transdermal patch off the patient.

7. An apparatus for delivering medication to a patient, comprising:
   (a) a transdermal patch having:
      a flexible member including a side adapted to face the patient and a plurality of through holes extending through said flexible member, said flexible member applying a medication to be administered to the patient through the skin of the patient, and
      a layer of adhesive applied to said flexible member on said side facing the patient; and
   (b) a removal device having:
      a solution including one of a solvent and an adhesive-neutralizing material,
      an absorbent dispensing material with said solution saturated therein, and
      a non-permeable member surrounding said solution and including a rigid member surrounding said absorbent dispensing material and a flexible membrane which is depressible to cause said solution to flow out of said adsorbent dispensing material;
   wherein said removal device is placed above said transdermal patch to enable said solution to penetrate said through holes to facilitate removal of said transdermal patch from the patient.

8. An apparatus for delivering medication to a patient, comprising
   (a) a transdermal patch including:
      a flexible permeable member having a side facing the patient and applying a medication to be administered to the patient through the skin of the patient, and
      a layer of adhesive applied to said flexible permeable member on said side facing the patient; and
   (b) a removal device having:
      a solution including one of a solvent and an adhesive-neutralizing material, and
      a non-permeable member surrounding said solution;
      wherein said removal device engages said transdermal patch to enable said solution to penetrate said flexible permeable member to facilitate removal of said transdermal patch from the patient.

9. The apparatus for delivering medication according to claim 8, wherein said removal device further comprises an absorbent dispensing material with said solution saturated therein.

10. The apparatus for delivering medication according to claim 8, further comprising a wedge coupled to said non-permeable member and adapted to push said transdermal patch off the patient.

11. An apparatus for delivering medication to a patient, comprising:

a) a transdermal patch having:
- a flexible permeable member including a side facing the patient and applying a medication to be administered to the patient through the skin of the patient, and
- a layer of adhesive applied to said flexible permeable member on said side facing the patient; and b) a removal device having:
- a solution including one of a solvent and an adhesive-neutralizing material,
- an absorbent dispensing material with said solution saturated therein, and
- a non-permeable member surrounding said solution and including a rigid member surrounding said absorbent dispensing material and a flexible membrane which is depressible to cause said solution to flow out of said absorbent dispensing material;

wherein said removal device is placed above said transdermal patch to enable said solution to penetrate said flexible permeable member to facilitate removal of said transdermal patch from the patient.

* * * * *